(12) United States Patent
Van Gilst et al.

(10) Patent No.: US 7,335,490 B2
(45) Date of Patent: Feb. 26, 2008

(54) USE OF ERYTHROPOIETIN FOR THE PREVENTIVE OR CURATIVE TREATMENT OF CARDIAC FAILURE

(75) Inventors: Wiekert Hendrikus Van Gilst, Haren (NL); Ronald Hendrik Peter Brus, Voorschoten (NL); Dirk Jan Van Veldhuisen, Paterswolde (NL); Robert Henk Henning, Loppersum (NL); Rudolf Allert De Boer, Boston, MA (US)

(73) Assignees: Crucell Holland B.V., Leiden (NL); Stichting Klinische Farmacologie Groningen, Groningen (NL)

( * ) Notice: Subject to any disclaimer, the term of this patent is extended or adjusted under 35 U.S.C. 154(b) by 142 days.

(21) Appl. No.: 10/500,913

(22) PCT Filed: Jan. 9, 2003

(86) PCT No.: PCT/NL03/00011

§ 371 (c)(1),
(2), (4) Date: Nov. 29, 2004

(87) PCT Pub. No.: WO03/057242

PCT Pub. Date: Jul. 17, 2003

(65) Prior Publication Data

US 2005/0075287 A1 Apr. 7, 2005

(30) Foreign Application Priority Data

Jan. 9, 2002 (WO) .................... PCT/NL02/00010

(51) Int. Cl.
C12P 21/06 (2006.01)
A61K 38/00 (2006.01)
C07K 14/00 (2006.01)

(52) U.S. Cl. .................... 435/69.1; 514/2; 530/350
(58) Field of Classification Search ............... 530/350; 514/12; 435/69.1, 7.1
See application file for complete search history.

(56) References Cited

U.S. PATENT DOCUMENTS 5,506,118 A * 4/1996 Berg et al. ................ 435/69.1

6,531,121 B2 * 3/2003 Brines et al. .............. 424/85.1

FOREIGN PATENT DOCUMENTS

WO  WO 00/61164     10/2000
WO  WO 01/82952 A2  11/2001
WO  WO 03/057242 A1  7/2003

OTHER PUBLICATIONS

Swedberg et al., Guidlines for the diagnosis and treatment of chronic feart failure: full text (update 2005) European Heart Journal published on the web on 2005 at http://www.escardio.org/NR/rdonlyres/8A2848B4-5DEB-41B9-9A0A-5B5A90494B64/0/guidelines_CHF_FT_2005.pdf, pp. 1-45.*
PCT International Search Report, PCT/NL03/00011, dated Apr. 24, 2003.
PCT International Preliminary Examination Report, PCT/NL03/00011, Dec. 10, 2003.
Silverberg et al., "The use of subcutaneous erythropoietin and intravenous iron for the treatment of the anemia of severe, resistant congestive heart failure improves cardiac and renal function and functional cardiac class, and markedly reduces hospitalizations," Journal of the American College of Cardiology, Jun. 2000, pp. 1737-1744, vol. 35, No. 7.
Mancini et al., "Erythropoietin improves exercise capacity in patients with heart failure," Circulation, Oct. 23, 2001, pp. II.428, vol. 104, No. 17 Supplement.
Akimoto et al., "Erythropoietin regulates vascular smooth muscle cell apoptosis by a phosphatidylinositol 3 kinase-dependent pathway," Kidney International, Jul. 2000, pp. 269-282, vol. 58, No. 1.
Westenfelder et al., "Anti-apoptotic, mitogenic and motogenic actions of erythropoietin on tubular cells protect renal function and accerlerate recovery from ischemic acute renal failure in rats," Journal of Investigative Medicine, Jan. 2001, pp. 59a, vol. 49, No. 1.
Arcasoy et al., "Erythropoeitin (EPO) stimulates angiogenesis in vivo and promotes wound healing," Blood, Nov. 16, 2001, pp. 822a-823a, vol. 98, No. 11, Part 1.
Krause et al., "Recombinant human erythropoietin stimulates angiogenesis in a novel in vitro assay of human myocardial tissue," Journal of the American College of Cardiology, Feb. 2001, pp. 236a, vol. 37, No. 2, Supplement A.

* cited by examiner

Primary Examiner—Robert B. Mondesi
(74) Attorney, Agent, or Firm—TraskBritt (57) ABSTRACT

Provided are uses of erythropoietin, or a derivative or functional analogue thereof, for the production of a medicament for the preventive or curative treatment of patients suffering from, or at risk of suffering from, cardiac failure.

4 Claims, 2 Drawing Sheets

SEQUENCE LISTING

<160> NUMBER OF SEQ ID NOS: 2

<210> SEQ ID NO 1
<211> LENGTH: 23
<212> TYPE: DNA

-continued

```
<213> ORGANISM: Artificial
<220> FEATURE:
<223> OTHER INFORMATION: Forward Primer

<400> SEQUENCE: 1
caggacacct acctggtatt gga                                          23

<210> SEQ ID NO 2
<211> LENGTH: 20
<212> TYPE: DNA
<213> ORGANISM: Artificial
<220> FEATURE:
<223> OTHER INFORMATION: Reverse Primer

<400> SEQUENCE: 2
caggcccaga gaggttctca                                              20
```

USE OF ERYTHROPOIETIN FOR THE PREVENTIVE OR CURATIVE TREATMENT OF CARDIAC FAILURE

CROSS-REFERENCE TO RELATED APPLICATIONS

This application is a national entry under 35 U.S.C. § 371 of International Patent Application PCT/NL03/00011, filed Jan. 9, 2003, published in English as International Patent Publication WO 03/057242 on Jul. 17, 2003, which claims the benefit under 35 U.S.C. § 119 of International Patent Application PCT/NL02/00010, filed Jan. 9, 2002.

TECHNICAL FIELD

The invention relates to the field of medicine. More particularly, the present invention relates to the treatment of hypoxia-related disorders in mammals and compounds and pharmaceutical preparations for use therein.

BACKGROUND

Cardiac failure is a chronic clinical syndrome characterized by the heart being unable to adequately pump blood throughout the body. Generally, it is caused by any disease or condition that causes loss of cardiac tissue, especially of the left ventricle. The most common causes include cardiac infarction, coronary artery disease, myocarditis, chemotherapy, alcoholism and cardiomyopathy. On the other hand, cardiac failure may be caused by diseases or conditions that require an excessive demand for cardiac output. The most common causes include hypertension, valvular heart diseases (most often mitral insufficiency and aortic stenosis) and disorders of the thyroid gland. The long-term extra demand on the heart will lead to a compensatory hypertrophy of the cardiomyocytes. As the capillary network does not extend, hypertrophy will lead to a relative ischemia because the diffusion pathway for oxygen will increase. Recently, the importance of the role of ischemia in cardiac failure has been put forward (Van den Heuvel et al., 2000).

Thus far, the treatment of patients suffering from ischemic heart disease and subsequent cardiac damage leading to heart failure has focused on early reperfusion. Although additional cell protection therapy might, in theory, limit the damage that is caused by myocardial ischemia and hence, reduce morbidity and mortality, no sufficient therapies exist to date.

Additional supportive therapy to protect the myocardium in acute ischemic conditions consists nowadays in administration of beta-blockers, calcium antagonists and nitrates. However, these therapies have a low efficacy and alternative and/or additional strategies are needed.

SUMMARY OF THE INVENTION

The present invention provides for the use of erythropoietin (EPO), or derivatives or functional analogues thereof, for the preparation of a medicament for the preventive and/or curative treatment of patients suffering from, or at risk of suffering from, cardiac failure. Treatment with EPO for these conditions can be beneficial, irrespective of their cause and nature. The invention also provides a method for treating a patient suffering from, or at risk of suffering from, cardiac failure, the method comprising a step of administering to the patient erythropoietin, or a derivative or functional analogue thereof. In one aspect of the invention, the patient suffering from heart failure is not anemic. Although recent clinical studies demonstrated the beneficial effects of EPO in patients with congestive heart failure (CHF) that also had anemia (Silverberg et al., 2000 and 2001), the person skilled in the art before the present invention would not treat patients with heart failure by using EPO in the absence of specific other indications for the use of EPO, such as anemia, kidney disease or leukemia. A certain fraction of CHF patients is anemic (low hematocrit/low hemoglobin percentage) and a correlation exists between the severity of the condition of CHF and the degree of anemia. When patients with anemia in CHF were treated with recombinant EPO, an improvement with respect to cardiac function, renal function and a decrease in the need for diuretics and hospitalization was observed (Silverberg et al. 2000 and 2001). Other publications (EP0813877; Mancini et al., 2001) also describe the use of EPO to raise the red blood cells and/or prevent anemia in the case of congestive heart failure. It appears that thus far, the improved condition of heart patients, upon treatment with EPO, was ascribed to the purposeful hematocrit elevation when patients had a medical indication to treat them with EPO, thus improving peripheral oxygenation by a mechanism unrelated to a change in cardiac function. The present invention for the first time discloses the use of EPO for the treatment of heart failure irrespective of whether the hematocrit value (red blood cell count) of the patient is lower than normal or not. This provides cardiac failure per se as a novel indication for the use of EPO. The present invention therefore provides for the use of EPO for treatment of patients with heart failure, wherein the patients do not necessarily have another indication besides heart failure, which would otherwise have warranted the treatment of such a patient with EPO based on the presently available knowledge.

In certain embodiments, the EPO, or derivative or functional analogue thereof, has been produced in a host cell expressing at least the E1A protein of an adenovirus, preferably in a host cell derived from a PER.C6™ cell.

The invention further provides erythropoietin, or a functional part, derivative and/or analogue thereof, for treatment of a patient suffering from, or at risk of suffering from, a chronic and/or acute coronary syndrome. Preferably, EPO has been recombinantly produced on a host cell that expresses at least the E1A protein of an adenovirus, more preferably on a host cell derived from a PER.C6™ cell. Although the use of EPO to protect the myocardium from acute ischemic injury has been described (see WO 00/61164, WO 01/82952), the EPO used may cause a concomitant significant increase in hematocrit values, which can be regarded as an undesired side effect for this application. The use of EPO derived from PER.C6™ or another E1A-expressing host cell, leads to less of this side effect and, therefore, is beneficial (see also PCT/NL02/00686 for the demonstration that EPO produced on PER.C6™ is functional but gives rise to less increase in hematocrit values when compared with a commercially available EPO preparation (EPREX®)).

The invention further provides the use of erythropoietin, or derivatives or functional analogues thereof, for the preparation of a medicament for the preventive and/or curative treatment of chronic and/or acute coronary syndromes. The invention also provides pharmaceutically effective preparations comprising EPO or a derivative or functional analogue thereof for such treatments.

Furthermore, the invention provides methods for treating a patient suffering from, or at risk of suffering from, undesirable effects of chronic or acute coronary syndromes, comprising the steps of administering to the patient erythropoietin or a derivative or analogue thereof in an amount sufficient to prevent or reduce the undesirable effects. Undesirable effects that may be decreased and/or inhibited by the compounds of the present invention include detrimental effects, such as apoptosis and/or necrosis of heart muscle cells. The effects on such cells most likely occur through the interaction of compounds of the invention with receptors present on such cells. Direct effects brought about by compounds of the present invention also include angiogenic effects through which certain hypoxia-related coronary syndromes are reduced in severity, both in acute as well as in chronic cases.

DETAILED DESCRIPTION

Erythropoietin (EPO), EPO derivatives and functional analogues are, when appropriate, hereinafter referred to as "EPO" for the sake of brevity. EPO is a protein well known for its role in differentiating hematopoietic stem cells into red blood cells, but it has many additional functions as well. This application reveals a novel EPO and EPO-receptor (EPO-R) system in the heart, which knowledge, according to the present invention, is converted into practical use by administering EPO to patients with heart failure.

Cardiac failure, also called heart failure, or chronic heart failure or congestive heart failure, is defined as a heart disease in which the heart is not able to pump blood at a rate required by the metabolizing tissues, or when the heart can do so only with an elevated filling pressure. Treatment of heart failure with EPO, according to the invention, includes treatment of patients having or being at risk of having cardiac infarction, coronary artery disease, myocarditis, chemotherapy, alcoholism, cardiomyopathy, hypertension, valvular heart diseases (most often mitral insufficiency and aortic stenosis) and disorders of the thyroid gland and the like.

According to the invention, a patient can be human, but may also include an animal with heart failure. Therefore, treatment according to the invention may pertain to humans as well as to other animal species.

A "non-anemic patient" as used herein, is a patient that has a hemoglobin value that is considered as being within the normal range, which value would not lead a physician to prescribe EPO to this patient. Until now, application of EPO has been restricted to the prevention or correction of anemia in specific patient populations, including the (pre)dialysis phase of chronic renal insufficiency, cytostatic therapy, premature infants and as preparation for autologous blood transfusion or surgical procedures with anticipated major blood loss. The general aim in such cases is to increase hemoglobin levels (Hb) by increasing the number of red blood cells (hematocrit) to a specific range by adapting standard dosage regimes to individual needs. Depending on the patient population, the optimal Hb level ranges from a lower limit of 6.5-7.5 mmol/L to an upper limit of 8.0-8.7 mmol/L.

According to one aspect of the invention, the EPO administered or formulated for use in the treatment of myocardial disease is EPO as may be isolated from any suitable source. Preferably, human EPO is recombinantly produced and isolated from a suitable recombinant host cell and/or from the culture medium. In the case of recombinant production, the host may suitably be chosen from any cell capable of recombinantly producing protein, such as bacterial host cells (e.g., E. coli, B. subtilis), yeast (e.g., S. cerevisiae, K. lactis), fungi (e.g., A. niger, Pichia), and mammalian cells (e.g., CHO, BHK cells) including human cells. According to one aspect of the invention, EPO is recombinantly produced in an immortalized human cell line, in particular PER.C6™ (ECACC deposit nr. 96022940). It is also possible to administer EPO in a gene-therapy setting according to the invention, for instance, by treating a patient with a vector comprising a nucleic acid sequence capable of expressing EPO when delivered to a target cell.

Derivatives of EPO refer to modifications of the source EPO, which may be urinary EPO or EPO recombinantly producible from a cDNA or gene sequence, wherein the expression product has one or more modifications relative to the source EPO, which modifications may be in the primary structure by substitution of one or more amino acid residues (such as in NESP), deletion, addition or relocation of one or more amino acid residues, or alterations in the post- or peri-translational modification of the protein backbone, such as hydroxylations, phosphorylations or glycosylations of amino acid residues, sulphur bridges, and the like.

Derivatives also encompass naturally or non-naturally occurring EPO variants coupled to non-EPO-related proteinaceous moieties or even to non-proteinaceous moieties. Derivatives of EPO are encompassed by the instant invention, as long as they interact with the EPO receptor and cause a reduction or prevention of the undesirable effects caused by chronic or acute coronary syndromes that include, but are not limited to, myocardial ischemia, myocardial infarction or heart failure, or caused by hypoxia conditions in the heart in general. As a measure for the occurrence of undesirable effects, the degree of apoptosis and/or necrosis in the heart tissue and/or the levels of purines in the coronary effluent circulation may be determined, or by any other means known in the art.

Functional analogues of EPO refer to molecules not necessarily derived from naturally on non-naturally occurring EPO that are capable of mimicking the interaction of EPO with its receptor, whereby the undesirable effects caused by chronic or acute myocardial ischemia or myocardial infarction, or hypoxia in the heart in general, are reduced and/or prevented. Such functional analogues may comprise peptidomimetics and/or non-peptidic molecules mimicking the idiotope interacting with the EPO-R. It will be understood by those of skill in the art that the functional analogue according to the invention need not necessarily interact with the same idiotope or in the same way, as long as it mimics the interaction of EPO with its receptor. Functional analogues may suitably be screened and selected from (synthetic) peptide libraries, phage or ribosome polypeptide display libraries, or small molecule libraries. Those of skill in the art are capable of screening for or designing functional analogues and test their functionality in assays disclosed herein. In addition to assays based on apoptosis and/or purine determination, other methods, such as methods towards measuring cell necrosis that are generally known in the art, may be used to test the functionality of the analogue in reducing and/or preventing the undesirable effects of hypoxia.

EPO may be administered to a mammal in any pharmaceutically acceptable form. Generally, EPO will be administered parenterally or subcutaneously (sc), but the way of administration may vary from time to time. Whenever it is needed to obtain a quick response, it may be desirable to add EPO in high dose form by means known to quickly deliver the pharmaceutical to the heart. Instances where this is clearly desired are, for example, where the patient suffers from acute syndromes such as acute myocardial ischemia, myocardial infarction or acute heart failure. In these circumstances, doses typically rise above the doses that are administered to human patients suffering from anemia or suffering from chronic coronary syndromes (Silverberg et al. 2000 and 2001). Normal doses that are administered to adult renal failure patients are in the range of 4000-7500 IU per week (80-100 kg body weight). These amounts are normally divided into three separate doses per week fan the commercially available epoetin alpha or EPREX® (EPO produced on CHO cells). Higher doses for the treatment of acute coronary disorders may be given daily or even more frequently. The maximum tolerable dose may have to be determined in order to prevent hematocrit values and hemoglobin concentrations to rise too sharply. Persons of ordinary skill know how to monitor hematocrit values and hemoglobin concentrations in patients to prevent undesired side effects, such as extreme high blood pressure that may occur in later stages of the treatment. These administration schemes contrast the schemes used by Silverberg et al. (2000 and 2001) to treat anemic patients that suffer from congestive heart failure, where administration of EPO was prolonged for weeks or even months. For acute coronary syndromes, it might not be necessary to prolong the treatment with the high doses for several months, since the protective effect is required instantly and undesired side effects might occur when such high doses are given for prolonged periods of time. In the case of chronic coronary syndromes including, but not limited to, myocardial ischemia or heart failure, lower doses may be administered during a longer time interval. Heart failure includes both acute heart failure syndromes, such as in the frame of myocardial infarction, but also reduced pumping of the heart in chronic cases. These applied doses are comparable to doses given to renal failure patients that suffer from the lack of EPO. Doses for non-acute hypoxia-related myocardial disorders may range from 10 to 10,000 IU per administration, preferably, 1000 to 2500 IU per administration (for an adult of 80-100 kg). Also, in this case, monitoring may be necessary to prevent unwanted side effects.

As disclosed in WO 00/63403, EPO can also be recombinantly produced on PER.C6™ cells. It was recently described (see patent application PCT/NL02/00686) that EPO thus produced leads to a significantly lower increase of the hematocrit value upon administration than similar doses of recombinant EPO currently commercially available (EPREX®). This appears mainly due to the specific post-translational modifications of the EPO thus produced, which appear related to the presence of at least the E1A sequence of an adenovirus in expressible format in the host cell used for recombinant production of EPO. A less pronounced increase in hematocrit value upon administration of EPO is beneficial for use according to the present invention. It is, therefore, a preferred embodiment of the present invention to use EPO according to the invention, whereby the EPO has been recombinantly produced in a host cell expressing at least the E1A protein, or a derivative or functional analogue thereof (see PCT/NL02/00686). Preferably, the host cell is a PER.C6™ cell. Such EPO can be used according to the invention for both chronic and acute coronary syndromes.

Novel formulations of EPO-like proteins are known in the art. The Novel Erythropoiesis Stimulating Protein (NESP) is known to be effective for longer periods of time due to its modified glycosylation pattern, which makes the administration schedule such that only a once a week dose is required to sort the effects that were formerly found with three doses a week of the original recombinant EPO protein. For the treatment of acute or chronic coronary syndromes, it might also be useful to apply NESP, which should be administered in a similar way as described above for EPO, namely, at higher (and possibly more frequent) doses in the case of acute coronary syndromes and at comparable (and equally frequent) doses in the case of chronic heart failure. It remains to be seen whether the modified glycosylation of NESP as compared to EPO has any differentiating effect on the EPO-R present on myocytes and endothelial cells in the blood vessels of the heart.

Pharmaceutically acceptable formulations according to the invention typically comprise EPO according to the invention, usually together with pharmaceutically acceptable excipients, diluents, solvents, and optionally, compounds acting in an additive or even synergistic fashion. Compounds of the latter category comprise compounds of the statin family, such as lovastatin, simvastatin, angiotensin-converting enzyme inhibitors (ACE-inhibitors), and the like.

It is worth noting that, according to the invention, the protective effect of EPO on hypoxia-induced myocardial damage, as determined by purine analysis in the coronary effluent and/or the degree of apoptotic cells in the myocardium, is observed within minutes after subcutaneous administration. It is difficult to imagine that this effect should be ascribed to EPO's known stimulating effect on angiogenesis, or to its hematopoietic effect for that matter, since these effects are typically not observed within the time frame of minutes, but rather days or even weeks. It is tempting, therefore, to speculate that the cell protective effect of EPO observed within minutes after administration is brought about by a direct intervention of EPO and tissues of, or in direct contact with, the myocardium. The fact that the EPO-R is found to be expressed on the cell surface of the myocytes (as is shown in this invention), strongly suggests that direct anti-apoptotic and anti-necrotic effects occur through the action of EPO on these receptors, while the direct angiogenic effects of EPO most likely occur through the EPO-R expressed on endothelial cells in the capillaries. This effect may occur in vitro as well as in vivo.

The invention will now be illustrated by the following examples.

EXAMPLES

Example 1

Detection of EPO and EPO-R in Normal Human and Rat Heart Tissue

It has been found that EPO and the EEO-R are expressed in fetal cardiac tissue (Juul et al. 1998). Despite the increasing body of literature on the expression of EPO and its receptor and the putative roles associated therewith, little, if anything, is known of the distribution of EPO and EPO-R in adult heart tissue.

Expression of EPO and EPO-R was examined by real-time RT-PCR, western blotting and immunohistochemistry on rat heart tissue and by western blotting and immunohistochemistry on human heart biopsies.

Rat Heart (Langendorff Set-Up)

For this, ischemic/reperfusion (I/R) experiments in isolated rat hearts suspended in a so-called Langendorff apparatus (Van Gilst et al. 1988) were performed with and without the administration of EPO, using methods generally known to persons skilled in the art.

Male Sprague Dawley Rats weighing approximately 300 grams (n=12) were divided into four experimental groups. Two groups received global cardiac ischemia by reducing coronary flow to 0.6 ml/minute for 30 minutes followed by reperfusion for 45 minutes. Two other groups were without ischemia. Within each of the groups, half of the rats were treated with EPO (10 U/ml) and half with saline. Rats were anesthetized and 500 U of heparin was injected in the tail vein. The heart was rapidly excised and the aorta was immediately retrogradely perfused by a modified Tyrode solution (glucose 10, NaCl 128.3, KCl 4.7, $NaHCO_3$ 20.2, $CaCl_2$, 1.35, $NaH_2PO_4$ 0.42, $MgCl_2$, 1.05; all mmol/liter) and was equilibrated with 95% $O_2$ and 5% $CO_2$. Perfusion pressure was maintained at 60 mmHg. Coronary flow (CF) was measured by a microprocessor, which controlled the perfusion pressure by adjusting the peristaltic perfusion pump. CF, heart rate (HR), and left ventricular peak pressure were monitored continuously. After equilibrating for five minutes, hearts were perfused for 20 minutes with EPO or saline before the I/R protocol started.

Real-Time RT-PCR

Total RNA was isolated from rat left ventricle and processed as described previously (Brundel et al., 1999). Briefly, cDNA was synthesized by incubating 1 μg of RNA in reverse transcription buffer, 200 ng of random hexamers with 200 U of Moloney Murine Leukemia Virus Reverse Transcriptase, 1 mmol/L of each dNTP, and 1 U of RNase inhibitor (Promega). Synthesis reaction was performed for 10 minutes at 20° C., 20 minutes at 42° C., 5 minutes at 99° C., and 5 minutes at 4° C. All products were checked for contaminating DNA. Fragments of EPO-R were amplified (Forward primer: CAGGACACCTACCTGGTATTGGA (SEQ ID NO:1); reverse primer: CAGGCCCAGAGAGGT-TCTCA (SEQ ID NO:2), Eurogentec, Belgium) with a GeneAmp® 5700 (Perkin-Elmer/ABI) employing a 40 cycle protocol consisting of 30 seconds at 94° C., 1 minute at 56° C. and 30 seconds at 72° C. After the last cycle, the 72° C. elongation step was extended to 5 minutes. The PCR products were detected using SYBR-green I. EPO-R was detected in cardiac samples of normal rat heart tissue and in tissue subjected in vitro to a 30 minute ischemic period irrespective of treatment with EPO.

Figure 1:
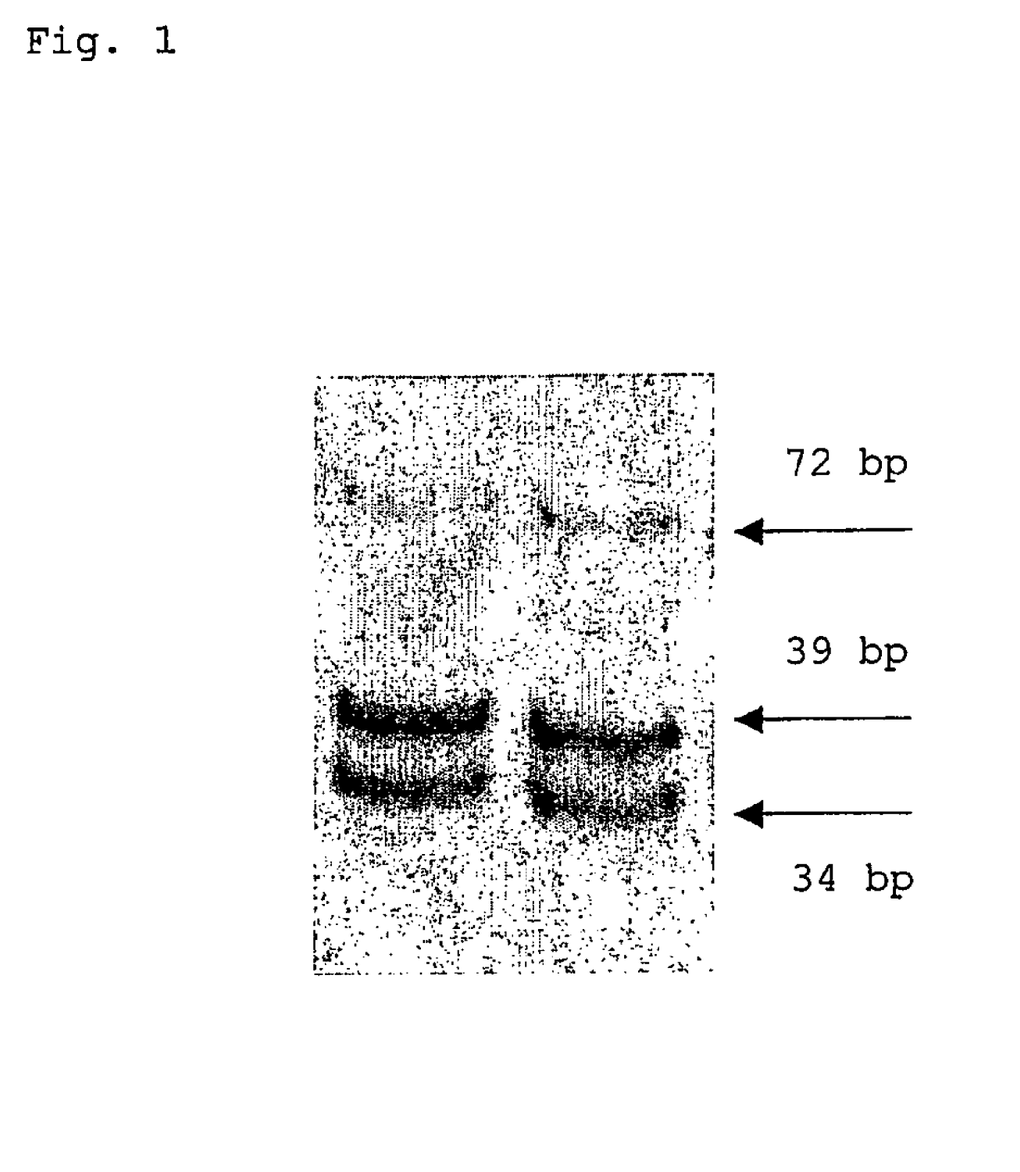
FIG. 1. Real Time RT-PCR of EPO-R mRNA. Specificity was checked with the use of restriction enzyme (NciI) for partial digestion of the 72 bp EPO-R product in expected fragments (39 bp and 34 bp).

To confirm specificity of the product, the amplified fragments were treated for 3 hours with the restriction enzyme NciI for partial digestion and separated on 2.5% agarose gels by gel-electrophoresis and stained with ethidium bromide. Restriction analysis confirmed splicing of the obtained product in two fragments of the expected size (34 and 39 bp, FIG. 1).

In contrast to EPO-R, we were unable to detect EPO mRNA in rat heart using the real-time RT-PCR method described by Neumcke et al. (1999) (while brain tissue was positive in the same PCR reaction).

Western Blotting

Figure 2:
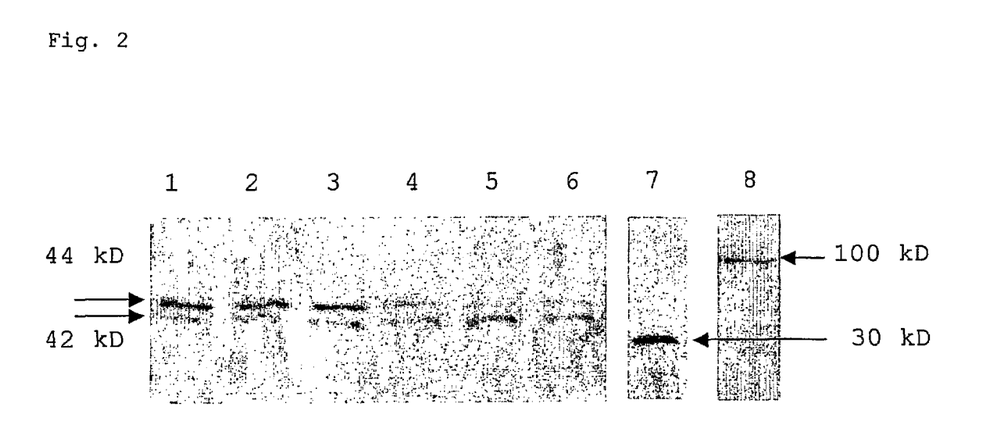
FIG. 2. Western blot. Lane 1-3: MAPK (pERK1=44 kD; pERK2=42 Kd) in sham treated hearts; lane 4-6: MAPK in EPO treated hearts; lane 7: EPO in sham treated heart; lane 8: EPO-R in sham treated heart.

Western blotting was performed according to standard methods (Brundel et al., 1999) on midpapillary slices from the left ventricle of rat heart, which were snap frozen in liquid nitrogen. In brief, frozen LV tissues (~50 mg) were homogenized in 1 ml of ice-cold protein lysis buffer and protease inhibitors. The homogenates were then centrifuged for 20 minutes at 4° C. at 14,000 rpm, and the supernatant was transferred into a clean tube and kept on ice. Protein concentration was determined by using a standard protein assay (Bio-Rad protein assay, Bio-Rad, Richmond, Calif.). Protein samples (50 μg) were subjected to SDS-PAGE on 7.5% acrylamide gels, and then transferred to PVDF membranes using a wet transfer unit (for 3 hours at 100 mA). The membranes were then blocked for 20 minutes with Tris-buffered saline containing 0.04% Tween 20 plus 5% non-fat dried milk, after which they were incubated for 3 hours with the primary antibody in Tris-buffered saline containing 0.04% Tween 20; 1:100 dilutions for the rabbit polyclonal anti-EPO-R antibody (C20, Santa Cruz Biotechnology, Santa Cruz, Calif.), anti-EPO antibody (H-162, Santa Cruz Biotechnology, Santa Cruz, Calif.), and 1:1000 dilutions for mouse monoclonal anti-phosphorylated ERK1/ERK2 antibody (#9106S, New England Biolabs, Beverly Mass.). Blots were incubated for 1 hour with HRP-conjugated secondary antibody prior to the development using an ECL kit (Amersham). Our results demonstrate that both EPO and the EPO-Receptor (EPO-R) are expressed on the protein level in Langendorff perfused hearts (FIG. 2). Expression levels of both EPO and EPO-R appear unaffected by ischemia reperfusion and by the application of EPO. In the next experiment, rat hearts were in vivo exposed to 10 U/ml EPO for 20 minutes. With the use of Western blotting, we found an increase in a phosphorylated MAPK, notably ERK1 and, to a lesser extent, in ERK2 (FIG. 2).

In summary, the Western blot demonstrates the presence of EPO and its receptor in cardiac tissue. We found EPO-R mRNA in cardiac tissue, but were unable to detect EPO mRNA, suggesting that EPO is not locally produced.

Finally, we found EPO to change levels of phosphorylated MAPK, especially pERK-1, thus implying a functional role of EPO-R in cardiac tissue. This may have important implications for the application of EPO in heart failure, as the extracellular signal-regulated kinases pathway (ERK1/2) has been recognized as an important regulator of cardiac hypertrophy and myocyte survival in response to hypertrophic agonists and stress stimuli (Bueno and Molkentin, 2002).

Immunohistochemistry

To evaluate the EPO and EPO-R expression pattern in rat heart tissue, complete mid-ventricular myocardial slices were obtained from the control rat group. Tissue sections were fixed and paraffin-embedded. Histological slices of approximately 3 μm were sectioned, dewaxed and rehydrated with graded ethanol. The sections were incubated with anti-EPO-R antibody (C20, Santa Cruz Biotechnology, Santa Cruz, Calif.) and with anti-EPO antibody (H-162, Santa Cruz Biotechnology, Santa Cruz, Calif.) using experimental methods well known to persons skilled in the art of immunohistochemistry. A two-step indirect peroxidase detection system was employed to visualize the expression pattern of EPO and EPO-R. All incubations were performed at room temperature and negative controls omitting the primary antibody were performed simultaneously. Using these immunohistochemistry in non-ischemic rat heart tissue, EPO expression was found in a number of rats (n=4), where the EPO expression appeared to be limited to arterioles and capillaries. No EPO expression was found in cardiomyocytes or in fibrocytes. The expression of EPO-R was also mostly restricted to arterioles and capillaries, although the cardiomyocytes showed a weak staining for EPO-R.

These findings further emphasize a possible role of EPO and EPO-R in angiogenesis.

Human Heart

Sections of formaline-fixed paraffin embedded human heart are obtained from routine autopsy cases (Dept. Pathology, Academic Hospital Groningen). Normal autopsy material harboring no cardiac pathology is obtained from at least 10 individuals. This material is used for Western blotting and immunohistochemistry as described above for the rat heart tissue.

Example 2

Effect of EPO in Acute Ischemic Events

The EPO-receptor (EPO-R) is found to be expressed at high concentrations in neuronal tissues (Digicaylioglu et al. 1995; Juul et al. 1997). The effects caused by (temporary) hypoxia due to cerebral ischemia may be mitigated by administering erythropoietin (EPO), as disclosed in WO 00/35475. Digicaylioglu and Liptyon (2001) have shown that preconditioning with EPO protects neurons in ischemic injury models and prevents apoptosis. As disclosed herein, EPO and the EPO-R are also expressed in cardiac tissue. Cardiac tissue that is susceptible to hypoxia may, therefore, benefit from treatment with EPO (see also e.g. WO 00/61164, WO 01/82952).

Apoptosis and the release of purines from the heart are measured to determine the effect of EPO in circumstances in which the heart tissue becomes ischemic. For this, ischemic/reperfusion (I/R) experiments in isolated rat hearts suspended in a so-called Langendorff apparatus (Van Gilst et al. 1988) are performed with and without the administration of EPO, using methods generally known to persons skilled in the art. The recombinant EPO is preferably obtained as described in WO 00/63403 using purification methods known to persons skilled in the art of protein production and isolation (see also PCT/NL02/00686). An alternative source of EPO is the commercially available epoetin alpha (EPREX®). Four separate experimental groups are used, each comprising eight Sprague Dawley (SD) rats. Each rat weighs approximately 250 grams. These groups are:
 SD rats without I/R, without EPO
 SD rats without I/R, with EPO
 SD rats with I/R, without EPO
 SD rats with I/R, with EPO The rats are anesthetized and the heart is rapidly excised. The aorta is immediately retrogradely perfused. Coronary flow (CF) is measured by a microprocessor, which controls the perfusion pressure by adjusting the peristaltic perfusion pump. CF, heart rate (HR), and left ventricular peak pressure are monitored continuously and stored in a computer database. After equilibrating for 15 minutes, baseline parameters are measured. Ischemia is induced by ligation of the left coronary artery for 15 minutes. Then, reperfusion is induced by releasing the ligature and the hearts are allowed to recover for 15 minutes.

Purine release from the heart has been shown to reflect myocardial damage (Van Jaarsveld et al. 1989). The coronary effluent dripping from the heart is collected for measurement of purines released by the myocardium. Baseline samples are collected after stabilization of the preparation, and coronary effluent is sampled after 15 minutes ischemia and after 15 minutes of reperfusion, and purines are measured by high-liquid performance chromatography (HPLC). The general trend is that initial purine values released from the coronary effluent from non-EPO-treated animals start off at higher values, while the decrease of purine over time appears to be slower, as compared to EPO-treated animals.

At the end of the experiments, hearts are weighed and a midpapillary slice from the left ventricle is cut out and fixed. The non-infarcted part of the heart (posterior wall, IV septum) is snap-frozen in liquid nitrogen. As described above, polyclonal antibodies against EPO and EPO-R are applied to determine the expression of both proteins.

Apoptosis is detected as follows. Sections from paraffin-embedded tissue blocks are placed on coated slides for in situ detection of apoptotic cells. Nuclear DNA fragments are visualized by an enzymatic reaction, using the ApopTag in situ apoptosis detection kit (Oncor, Gaithersburg USA) following the manufacturer's instructions. Number and distribution of stained cells, morphologic nuclear features and intensity of staining are evaluated.

Example 3

Effect of EPO in Chronic Ischemia Model Systems

Myocardial infarction is induced in rats and the role of EPO, which is administered in vivo, is determined by measuring Left Ventricular Pressure (LVP), infarct size, apoptosis and microvascular density. For this, SD rats are either sham-operated (SH) or myocardial infarcted (MI) and treated with EPO (see above) in a concentration of 400 units per kg sc, or with saline, every day for four weeks. Four separate experimental groups are used, each comprising eight SD rats. Each net weighs approximately 250 grams. The groups used are:
 SD rats with sham operation, without EPO
 SD rats with sham operation, with EPO
 SD rats with myocardial infarction, without EPO
 SD rats with myocardial infarction, with EPO The myocardial infarction model has been described elsewhere (Pinto et al. 1993). In brief, anesthesia is induced and a left-sided thoracotomy is performed and MI is created by ligating the left coronary artery with a 6-0 silk suture, 1-2 mm after the bifurcation with the aorta. In sham-operated rats, the same operation will be executed, without ligating the suture.

The Left Ventricular (LV) function is determined as follows. After four weeks, rats are anesthetized and the right carotid artery is cannulated with a pressure transducer catheter. After a 3 minute period of stabilization, maximal LVP, LV end-diastolic pressure (LVEDP) and heart rate are recorded. Hereafter, the catheter is withdrawn to measure systolic blood pressure in the aortic root. As indices of global contractility and relaxation, the maximal rates of increase and decrease in LVP (systolic dP/dt and diastolic dP/dt) is determined, which will be further corrected for peak systolic LVP.

The infarct size is determined by histological analysis by staining for LDH using general methods known to persons skilled in the art. Total epicardial and endocardial circumference of the left ventricle and epicardial and endocardial scar length of the infracted area are determined by means of a computerized planimeter. Infarct size is calculated by dividing the sum of the scar lengths by the sum of the total circumferences, as previously described in detail (Pinto et al. 1993). Furthermore, apoptosis is measured as described above.

The microvascular density is determined as follows (Loot et al., 2002). The paraffin-embedded LV slice is cut and stained with hematoxylin-eosin for histological analysis to calculate infarct size and with RECA-1 antibody to visualize microvessels using methods known to persons skilled in the art. Microvessel density per mm$^2$ is measured in the spared myocardium (opposing the infarction, usually ventricular septum or posterior wall). From each rat, seven to ten microscopic high-power fields with transversely sectioned myocytes are digitally recorded with appropriate software. The microcirculation is defined as vessels beyond the third order arterioles, with a diameter of 150 μm or less, supplying tissue between arterioles and venules. Myocyte surface areas are measured by morphometry, selecting myocytes with a central nucleus with the largest possible surface area with image analysis software (Loot et al., 2002).

Example 4

Determination of EPO and EPO-R Levels in Chronic Ischemia in Human Heart

The expression levels of EPO and EPO-R are determined by the level of mRNA, using a semi-quantitative Reverse Transcriptase Polymerase Chain Reaction (RT-PCR) technique. For this, total RNA is isolated using the acid guanidium thiocyanate lysis method (Chomczynski and Sacchi 1987). The RNA is obtained from tissue from patients with ischemic heart failure. The tissue is removed during cardiac catheterization by right ventricular endomyocardial biopsy from the right jugular or femoral vein, using standard techniques known to persons skilled in the art. Reverse transcription of RNA and amplification of cDNA is performed by RT-PCR. The cDNA of interest and the cDNA of the housekeeping enzyme GAPDH are detected by real-time RT-PCR as described above.

REFERENCES

Brundel B J J M, Van Gelder I C, Henning R H, et al. (1999). Gene expression of proteins influencing the calcium homeostasis in patients with persistent and paroxysmal atrial fibrillation. *Cardiovasc. Res.* 42:443-454.

Bueno O F, Molkentin J D (2002). Involvement of extracellular signal-regulated kinases ½ in cardiac hypertrophy and cell death. *Circ. Res.* 91:776-781.

Chomczynski P and Sacchi N (1987). Single step method of RNA isolation by acid guanidinium thiocyanate-phenol-chloroform extraction. *Anal. Biochem.* 162:156-159.

Digicaylioglu M, Bichet S, Marti H H, Wenger R H, Rivas L A, Bauer C and Gassmann H (1995). Localization of specific erythropoietin binding sites in defined areas of the mouse brain. *Proc. Natl. Acad. Sci. USA* 92:3717-3720.

Digicaylioglu H and Liptyon S A (2001). Erythropoietin-mediated neuroprotection involves cross-talk between Jak2 and NF-kB signaling cascades. *Nature* 412:641-645.

Juul S E, Harcum J, Li Y and Christensen R D (1997). Erythropoietin is present in the cerebrospinal fluid of neonates. *J. Pediatr.* 130:428-430.

Juul S E, Yachnis A T and Christensen R D (1998). Tissue distribution of erythropoietin and erythropoietin receptor in the developing human fetus. *Early Hum. Dev.* 52:235-249.

Mancini D, et al. (2001). Erythropoietin improves exercise capacity in patients with heart failure. *Circulation* 104 (no. 17 suppl): II.438.

Loot A E, Roks A J, Henning R H, Tio R A, Suurmeijer A J, Boomsma F, van Gilst W H (2002). Angiotensin-(1-7) attenuates the development of heart failure after myocardial infarction in rats. *Circulation* 105:1548-1550.

Neumcke I, Schneider B, Fandrey J, Pagel H (1999). Effects of pro- and antioxidative compounds on renal production of rythropoietin. *Endocrinology* 140:641-645.

Pinto Y M, De Smet B G, Van Gilst W H, et al. (1993). Selective and time-related activation of the cardiac rennin-angiotensin system after experimental heart failure: relation to ventricular function and morphology. *Cardiovasc. Res.* 27:1933-1938.

Silverberg D S, Wexler D, Blum M, Keren G, Sheps D, Leibovitch E, Brosh D, Laniado S, Schwartz D, Yachnin T, Shapira I, Gavish D, Baruch R, Koifman B, Kaplan C, Steinbruch S and Iaina A (2000). The use of subcutaneous erythropoietin and intravenous iron for the treatment of the anemia of severe, resistant congestive heart failure improves cardiac and renal function and functional cardiac class, and markedly reduces hospitalizations. *J. Am. Coll. Cardiol.* 35:1737-1744.

Silverberg D S, Wexler D, Sheps D, et al. (2001). The effect of correction of mild anemia in severe, resistant congestive heart failure using subcutaneous erythropoietin and intravenous iron: a randomized controlled study. *J. Am. Coll. Cardiol.* 37:1775-1780.

Van den Heuvel A F, van Veldhuisen D J, van den Wall E E, Blanksma P K, Siebelink H M, Vaalburg W M, van Gilst W H, Crijns H J (2000). Regional myocardial blood flow reserve impairment and metabolic changes suggesting myocardial ischemia in patients with idiopathic dilated cardiomyopathy. *J. Am. Coll. Cardiol.* 35:19-28.

Van Gilst W H, Scholtens E, De Graeff P A, et al. (1988). Differential influences of angiotensin converting enzyme inhibitors on the coronary circulation. *Circulation* 77:124-129.

Van Jaarsveld H, Barnard H C, Barnard S P, et al. (1989). Purine and oxypurine production in mitochondria of ischemic and reperfused myocardium. *Enzyme* 42:136-144.

What is claimed is:

1. A method of treating a patient suffering from chronic heart failure, the method comprising:
    producing erythropoietin (EPO) in an isolated host cell expressing at least the Early Region 1A (E1A) protein of an adenovirus, wherein said host cell is a cell as deposited under European Collection of Animal Cell Cultures (ECACC) no. 96022940;
    preparing a medicament comprising said EPO for the treatment of a patient suffering from chronic heart failure; and
    administering said medicament to said patient.

2. The method according to claim 1, wherein said patient is non-anemic.

3. The method according to claim 1, wherein the subject is non-anemic.

4. A method of treating a subject suffering from chronic heart failure, the method comprising:
    administering to the subject erythropoietin (EPO), wherein the EPO has been produced by a process comprising:
        expressing EPO in an isolated host cell that expresses Early Region 1A (E1A) protein of an adenovirus, wherein said host cell is a cell as deposited under European Collection of Animal Cell Cultures (ECACC) no. 96022940.

* * * * *

UNITED STATES PATENT AND TRADEMARK OFFICE
CERTIFICATE OF CORRECTION

| | |
|---|---|
| PATENT NO. | : 7,335,490 B2 |
| APPLICATION NO. | : 10/500913 |
| DATED | : February 26, 2008 |
| INVENTOR(S) | : Wiekert Hendrikus Van Gilst et al. |

It is certified that error appears in the above-identified patent and that said Letters Patent is hereby corrected as shown below:

On the title page:
In ITEM (56) References Cited
OTHER PUBLICATIONS
Page 1, 2$^{nd}$ Column, 1$^{st}$ line          change "Guidlines" to --Guidelines--

In the specification:

| | | |
|---|---|---|
| COLUMN 3, | LINE 17, | change "(NciI)" to --*(Nci*I)-- |
| COLUMN 3, | LINE 21, | change "Kd)" to --kD)-- |
| COLUMN 5, | LINE 17, | change "fan" to --from-- |
| COLUMN 6, | LINE 49, | change "in vitro as well as in vivo." to --*in vitro* as well as *in vivo*.-- |
| COLUMN 6, | LINE 60, | change "EEO-R" to --EPO-R-- |
| COLUMN 7, | LINE 21, | change "NaH$_2$PO$_4$0.42," to --NaH$_2$PO$_4$ 0.42,-- |
| COLUMN 7, | LINE 50, | change "in vitro" to --*in vitro*-- |
| COLUMN 7, | LINE 54, | change "NciI" to --*Nci*I-- |
| COLUMN 8, | LINE 28, | change "in vivo" to --*in vivo*-- |
| COLUMN 10, | LINE 2, | change "high-liquid performance" to --high-performance liquid-- |
| COLUMN 10, | LINE 17, | change "(Oncor, Gaithersburg USA)" to --(Oncor Inc, Gaithersburg, MD USA)-- |
| COLUMN 10, | LINE 27, | change "in vivo," to --*in vivo*,-- |
| COLUMN 10, | LINE 34, | change "net" to --rat-- |
| COLUMN 12, | LINE 19, | change "rythropoietin." to --erythropoietin.-- |

In the claims:

| | | |
|---|---|---|
| CLAIM 3, COLUMN 14, | LINE 21, | change "3. The method according to claim 1," to --4. The method according to claim 3,-- |
| CLAIM 4, COLUMN 14, | LINE 23, | change "4. A method" to --3. A method-- |

Signed and Sealed this
First Day of March, 2011

David J. Kappos
*Director of the United States Patent and Trademark Office*